(12) United States Patent
Baek et al.

(10) Patent No.: US 12,350,078 B2
(45) Date of Patent: Jul. 8, 2025

(54) X-RAY IMAGING DEVICE AND CONTROL METHOD THEREOF

(71) Applicant: LG ELECTRONICS INC., Seoul (KR)

(72) Inventors: Seungchan Baek, Seoul (KR); Sangjun Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 307 days.

(21) Appl. No.: 18/026,711

(22) PCT Filed: Aug. 24, 2021

(86) PCT No.: PCT/KR2021/011316
§ 371 (c)(1),
(2) Date: Mar. 16, 2023

(87) PCT Pub. No.: WO2022/059950
PCT Pub. Date: Mar. 24, 2022

(65) Prior Publication Data
US 2023/0337994 A1 Oct. 26, 2023

(30) Foreign Application Priority Data

Sep. 17, 2020 (KR) .................. 10-2020-0119821
Aug. 18, 2021 (KR) .................. 10-2021-0108880

(51) Int. Cl.
*A61B 6/00* (2024.01)
*A61B 6/03* (2006.01)
*A61B 6/40* (2024.01)

(52) U.S. Cl.
CPC ............ *A61B 6/4007* (2013.01); *A61B 6/032* (2013.01)

(58) Field of Classification Search
CPC .. A61B 6/02; A61B 6/025; A61B 6/03; A61B 6/42; A61B 6/542; A61B 6/54; A61B 6/545
See application file for complete search history.

(56) References Cited

U.S. PATENT DOCUMENTS

2010/0303323 A1* 12/2010 Matsumoto .......... A61B 6/4429
382/131

FOREIGN PATENT DOCUMENTS

| JP | 8-84295 A | 3/1996 |
|---|---|---|
| JP | 10-118055 A | 5/1998 |
| JP | 2002-320608 A | 11/2002 |

(Continued)

*Primary Examiner* — Don K Wong
(74) *Attorney, Agent, or Firm* — Birch, Stewart, Kolasch & Birch, LLP

(57) ABSTRACT

An X-ray imaging device and a control method thereof are provided. The X-ray imaging device according to an embodiment of the present invention comprises: an X-ray generator including at least one X-ray source which radiates X-rays; an X-ray detector which detects X-rays radiated from the X-ray generator to generate multiple pieces of projection data; and a processor which controls the X-ray generator to be in one mode among a first mode in which the X-ray generator radiates X-rays for a first radiation time and a second mode in which the X-ray generator radiates X-rays for a second radiation time corresponding to half of the first radiation time, and generates a tomography image on the basis of the multiple pieces of projection data generated through the X-ray detector.

20 Claims, 11 Drawing Sheets

(56) References Cited

FOREIGN PATENT DOCUMENTS

| | | |
|---|---|---|
| JP | 2015-73554 A | 4/2015 |
| KR | 10-2011-0047272 A | 5/2011 |
| KR | 10-2014-0013403 A | 2/2014 |

\* cited by examiner

X-RAY IMAGING DEVICE AND CONTROL METHOD THEREOF

CROSS-REFERENCE TO RELATED APPLICATION

This application is the National Stage filing under 35 U.S.C. 371 of International Application No. PCT/KR2021/011316, filed on Aug. 24, 2021, which claims the benefit of earlier filing date of and rights of priority to Korean Application No. 10-2020-0119821 filed in the Republic of Korea on Sep. 17, 2020, and Korean Application No. 10-2021-0108880 filed in the Republic of Korea on Aug. 18, 2021, the entire contents of all these applications being hereby incorporated by reference into the present application.

BACKGROUND

Technical Field

The present disclosure relates to an X-ray imaging device and a method of processing an X-ray image, and more particularly, to an X-ray imaging device configured to generate a tomography image on a basis of multiple pieces of projection data and a method of processing an X-ray image.

Discussion of the Related Art

A two-dimensional (2D) X-ray image captured by an X-ray imaging system is an image in which X-rays are projected toward a subject to be X-ray imaged in one direction. Accordingly, as the X-rays are projected onto the subject in one direction, a problem such that an image of the subject is covered and overlapped occurs.

To solve this problem, a computed tomography (CT) device is provided as a representative device configured to capture an image of a subject by radiating X-rays toward a patient. Among medical image processing devices, a tomography device, i.e., a CT device has an advantage of providing a cross-sectional image of a subject and presenting an image in which internal structures (e.g., an organ such as a kidney, a lung, etc.) of a subject do not overlap each other compared to a general X-ray device. Thus, the CT device is widely used for precise diagnosis of diseases.

However, since the CT device captures X-ray images by projecting X-rays on a subject in various directions for several times, it has a problem such as an increase in a dose of X-ray radiation exposure.

Recently, a tomosynthesis X-ray imaging system configured to implement a three-dimensional (3D) image with a low dose radiation compared to the CT device is being introduced.

The tomosynthesis X-ray imaging system uses a technique of acquiring a 3D image with a low dose radiation compared to the CT device, and may remove an overlapping or covering effect by providing a tomography image for each depth.

Generally, the tomosynthesis X-ray imaging system rotationally moves an analog X-ray generator in an arch form with reference to a certain rotating shaft and moves or rotates an X-ray detector in correspondence with a position of the analogue X-ray generator to capture several X-ray images to thereby implement a 3D image through a reconstruction algorithm.

The tomosynthesis X-ray imaging system acquires an image by performing rotational movement using the analog X-ray generator installed together with a rail on a ceiling, and thus, has such a disadvantage that a size of a whole system is increased and a space to be ensured for the installation is increased.

Accordingly, there is a need for an X-ray imaging system such that a space to be occupied by the X-ray imaging system is minimized, and convenience of installation of the X-ray imaging system is ensured or movement thereof is allowed.

SUMMARY OF THE DISCLOSURE

Technical Problem

Therefore, to obviate those problems, an aspect of the detailed description is to provide an X-ray imaging device configured to reconstruct a two-dimensional (2D) or three-dimensional (3D) type tomography image by reconstructing multiple pieces of projection data obtained from images captured using the X-ray imaging device, and a method of processing an X-ray image.

An aspect of the detailed description is to provide an X-ray imaging device that may generate a tomography image while reducing an X-ray dose, and a method of processing an X-ray image.

An aspect of the detailed description is to provide an X-ray imaging device that may shorten X-ray imaging time while reducing an X-ray dose, and a method of processing an X-ray image.

An aspect of the detailed description is to provide an X-ray imaging device that may reduce a time of a single radiation exposure when an X-ray is radiated, and a method of processing an X-ray image.

Solution to Problem

To achieve these and other advantages and in accordance with the purpose of the present invention, as embodied and broadly described herein, there is provided an X-ray imaging device including: an X-ray generator including at least one X-ray source configured to radiate X-rays; an X-ray detector configured to generate multiple pieces of projection data by detecting X-rays radiated from the X-ray generator; and a processor configured to control the X-ray generator to be in one mode among a first mode in which the X-ray generator radiates X-rays during a first radiation time and a second mode in which the X-ray generator radiates X-rays during a second radiation time corresponding to half of the first radiation time, and generate a tomography image on a basis of the multiple pieces of projection data generated through the X-ray detector.

According to embodiments, the processor may radiate X-rays at a constant time interval in the first mode and in the second mode, control the X-ray generator to radiate the X-rays during the first radiation time at the constant time interval in the first mode, and control the X-ray generator to radiate the X-rays during the second radiation time corresponding to half of the first radiation time at the constant time interval in the second mode.

According to embodiments, the X-ray source may include a plurality of light-emitting devices configured to output X-rays, the X-ray source may include a plurality of gate lines configured to cause the plurality of light-emitting devices to emit light, and in the second mode, the processor may apply a signal to even gate lines among the plurality of gate lines during a first period to radiate X-rays during the second radiation time corresponding to half of the first radiation time, and apply a signal to odd gate lines among the plurality of gate lines during a second period that follows the first period.

According to embodiments, the processor may, in the second mode, acquire a first tomography image on a basis of projection data obtained through the X-ray detector during the first period, acquire a second tomography image on a basis of projection data obtained through the X-ray detector during the second period, and generate a final tomography image using the first and second tomography images.

According to embodiments, the processor may control the X-ray generator in a third mode in which X-rays are radiated during the second radiation time at a time interval corresponding to half of the constant time interval.

According to embodiments, the processor may control the X-ray generator to radiate X-rays for a same number of times in the first mode and the third mode.

According to embodiments, the processor may control the X-ray generator to radiate X-rays in the third mode for a number of times corresponding to twice a number of times of radiation in the first mode.

According to other embodiments, there is provided a method of controlling an X-ray imaging device, the method including: controlling an X-ray generator in one mode among a first mode in which the X-ray generator radiates X-rays during a first radiation time and a second mode in which the X-ray generator radiates X-rays during a second radiation time corresponding to half of the first radiation time; and generating a tomography image on a basis of multiple pieces of projection data generated through an X-ray detector.

According to embodiments, the controlling may include radiating X-rays at a constant time interval in the first mode and in the second mode, controlling the X-ray generator to radiate the X-rays during the first radiation time at the constant time interval in the first mode, and controlling the X-ray generator to radiate the X-rays during the second radiation time corresponding to half of the first radiation time at the constant time interval in the second mode.

According to embodiments, the X-ray source may include a plurality of light-emitting devices configured to output X-rays, and the X-ray source may include a plurality of gate lines configured to cause the plurality of light-emitting devices to emit light, wherein the controlling includes, in the second mode, applying a signal to even gate lines among the plurality of gate lines during a first period to radiate X-rays during the second radiation time corresponding to half of the first radiation time, and applying a signal to odd gate lines among the plurality of gate lines during a second period that follows the first period.

According to embodiments, the controlling may include, in the second mode, acquiring a first tomography image on a basis of projection data obtained through the X-ray detector during the first period, acquiring a second tomography image on a basis of projection data obtained through the X-ray detector during the second period, and generating a final tomography image using the first and second tomography images.

According to embodiments, a dose of X-rays radiated toward a subject in the second mode may correspond to half of a dose of X-rays radiated toward the subject in the first mode.

According to embodiments, the method may further include controlling the X-ray generator in a third mode in which X-rays are radiated during the second radiation time at a time interval corresponding to half of a constant time interval.

According to embodiments, X-rays may be radiated for a same number of times in the first mode and the second mode.

According to embodiments, the method may further include controlling the X-ray generator to radiate X-rays in the third mode for a number of times corresponding to twice a number of times of radiation in the first mode.

Advantageous Effects of Invention

In accordance with the detailed description, the present disclosure may provide an X-ray imaging method and device optimized for acquiring a tomography image while reducing a dose of X-ray radiation exposure to a subject during X-ray imaging.

Further scope of applicability of the present disclosure will become apparent from the following detailed description. It should be understood, however, that the detailed description and specific examples, such as the preferred embodiment of the invention, are given by way of illustration only, since various changes and modifications within the spirit and scope of the invention will be apparent to those skilled in the art.

DETAILED DESCRIPTION OF THE EMBODIMENTS

Description will now be given in detail according to exemplary embodiments disclosed herein, with reference to the accompanying drawings. For the sake of brief description with reference to the drawings, the same or equivalent components may be provided with the same or similar reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In describing the present disclosure, if a detailed explanation for a related known technology or construction is considered to unnecessarily divert the gist of the present disclosure, such explanation has been omitted but would be understood by those skilled in the art. The accompanying drawings are used to help easily understand the technical idea of the present disclosure and it should be understood that the idea of the present disclosure is not limited by the accompanying drawings. The idea of the present disclosure should be construed to extend to any alterations, equivalents and substitutes besides the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the another element or intervening elements may also be present. In contrast, when an element is referred to as being "directly connected with" another element, there are no intervening elements present.

A singular representation may include a plural representation unless it represents a definitely different meaning from the context.

Terms such as "include" or "has" are used herein and should be understood that they are intended to indicate an existence of several components, functions or steps, disclosed in the specification, and it is also understood that greater or fewer components, functions, or steps may likewise be utilized.

Figure 1:
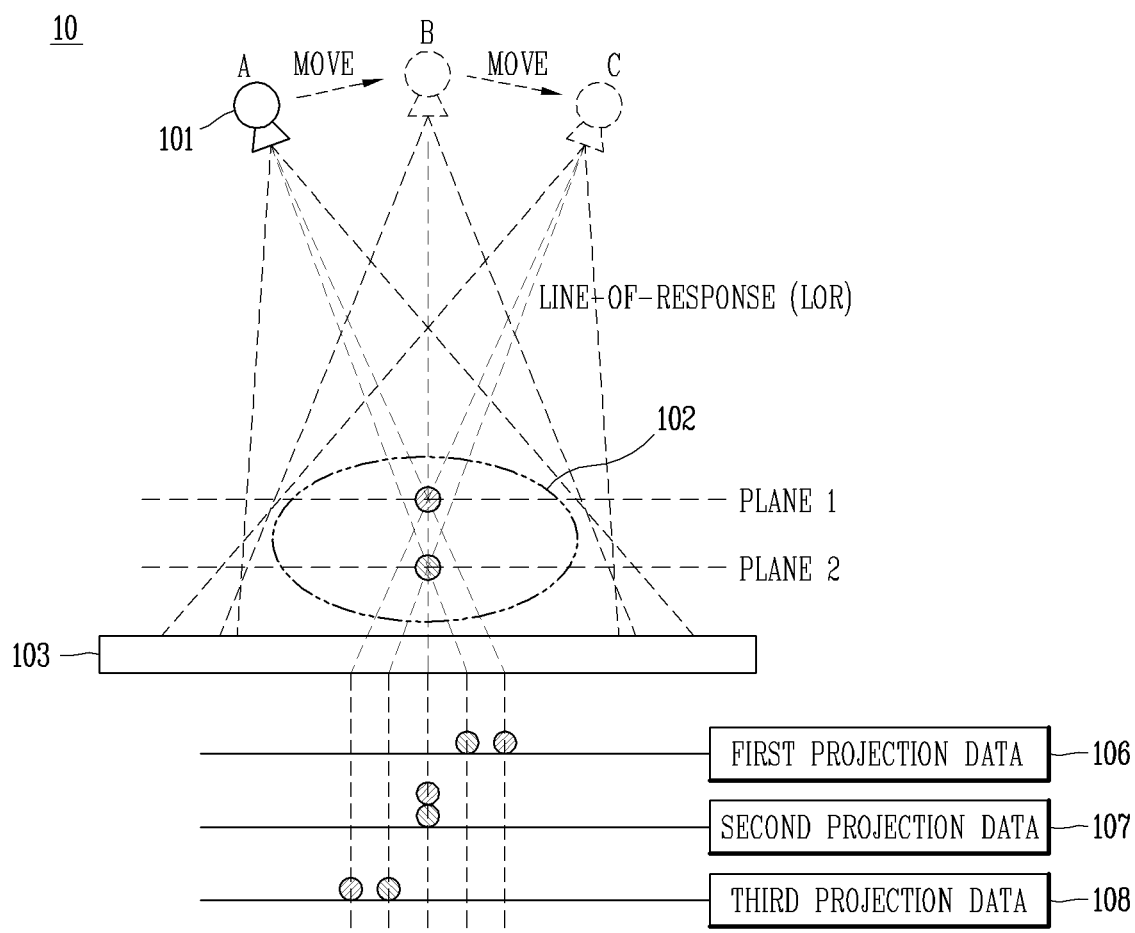
FIG. 1 is a diagram for explaining a tomosynthesis system in the related art.

FIG. 1 is a diagram for explaining a tomosynthesis system in the related art.

A tomosynthesis system 10 in the related art radiates X-rays toward a subject 102 to be imaged, as an X-ray generator 101 rotationally moves by about to 50 degrees relative to a certain rotating shaft. An X-ray detector 103 may generate an electrical signal corresponding to a transmitted X-ray dose.

When the X-ray generator 101 rotationally moves to radiate the X-rays toward the subject 102 to be imaged, projected X-rays may be detected by the X-ray detector 103 to generate multiple pieces of projection data 106, 107, and 108.

With reference to a first plane Plane 1 and a second plane Plane 2 of the subject 102 to be imaged, each of a first point and a second point may be projected by X-rays emitted from the X-ray generator 101 to be mapped with each of the multiple pieces of projection data 106, 107, and 108.

In this case, the first point and the second point mapped with each of the multiple pieces of projection data 106 to 108 may be mapped to be different from each other due to a change in an incident angle according to rotational movement of the X-ray generator 101. Accordingly, there is an additional need to reconstruct the subject 102 to be imaged, as a two-dimensional (2D) or three-dimensional (3D) X-ray tomography image, on a basis of the multiple pieces of projection data 106 to 108.

Figure 2:
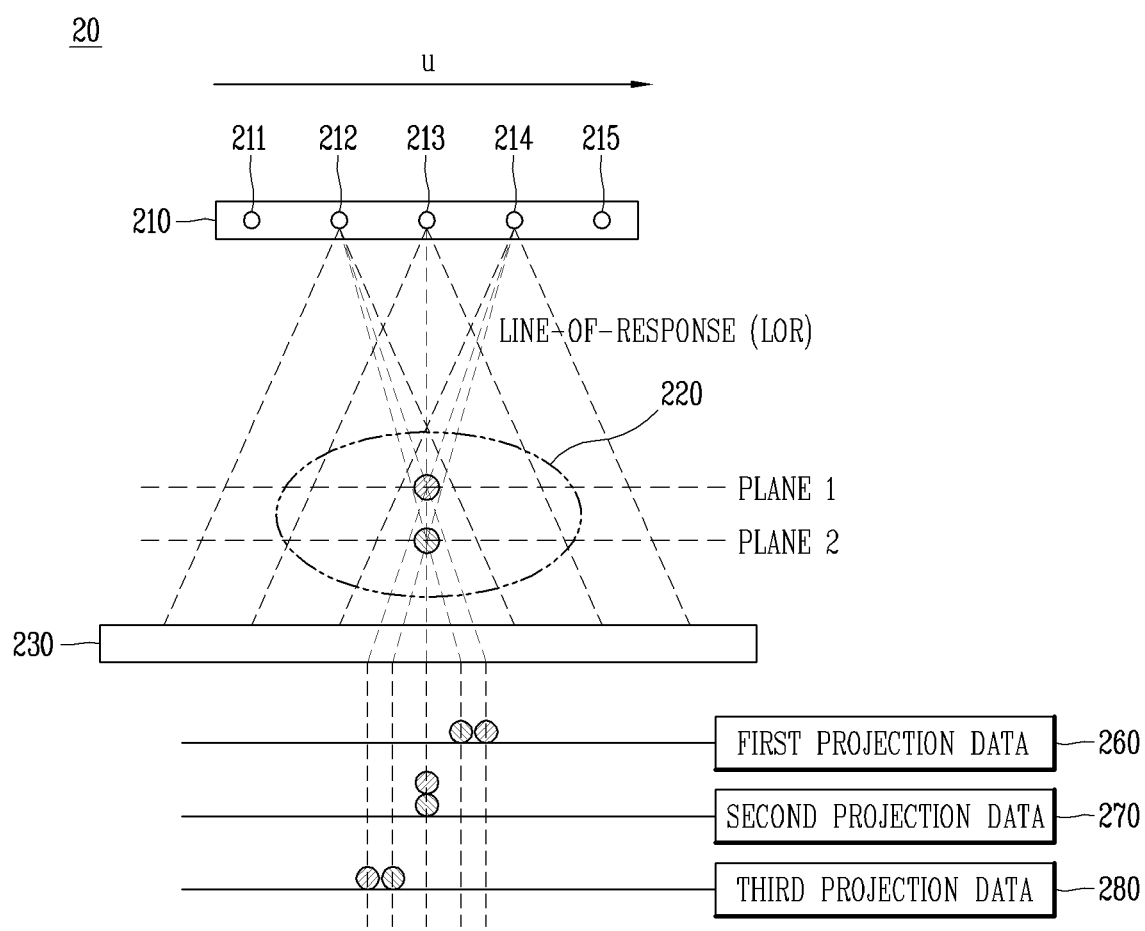
FIG. 2 is a diagram for explaining an X-ray imaging device according to an embodiment of the present disclosure.

FIG. 2 is a diagram for explaining an X-ray imaging device according to an embodiment of the present disclosure.

An X-ray imaging device 20 includes an X-ray generator 210 in which a plurality of X-ray sources 211, 212, 213, 214, and 215 are arranged. The X-ray sources 211 to 215 are turned on or off to emit and radiate X-rays toward a subject 220 to be imaged.

An X-ray detector 230 may generate an electrical signal corresponding to a transmitted X-ray dose. An X-ray source may emit X-rays using an electric field method.

Meanwhile, the X-ray imaging device 20 may use a horizontal moving method instead of a rotational movement of the tomosynthesis system 10 in the related art. For example, the X-ray imaging device 20 may control X-rays to be emitted sequentially by first to third X-ray sources, i.e., the X-ray sources 212 to 214.

With reference to the first plane Plane 1 and the second plane Plane 2 of the subject 220 to be imaged, each of a first point and a second point may be captured by being mapped with each of multiple pieces of projection data 260, 270, and 280.

In this case, the first point and the second point may be mapped with each of the multiple pieces of projection data 260 to 280 due to horizontal movement according to turning on or off of each of the X-ray resources 211 to 215 in the X-ray generator 210.

Accordingly, there is an additional need to reconstruct the subject 220 to be imaged as a 2D or 3D X-ray tomography image on a basis of a plurality of X-ray images, i.e., the multiple pieces of projection data 260 to 280.

In this case, unlike the tomosynthesis system 10 in the related art, a tomography image needs to be generated by reconstructing multiple pieces of projection data by reflecting characteristics obtained as on or off operations of the X-ray sources are performed in a horizontal direction.

Figure 3:
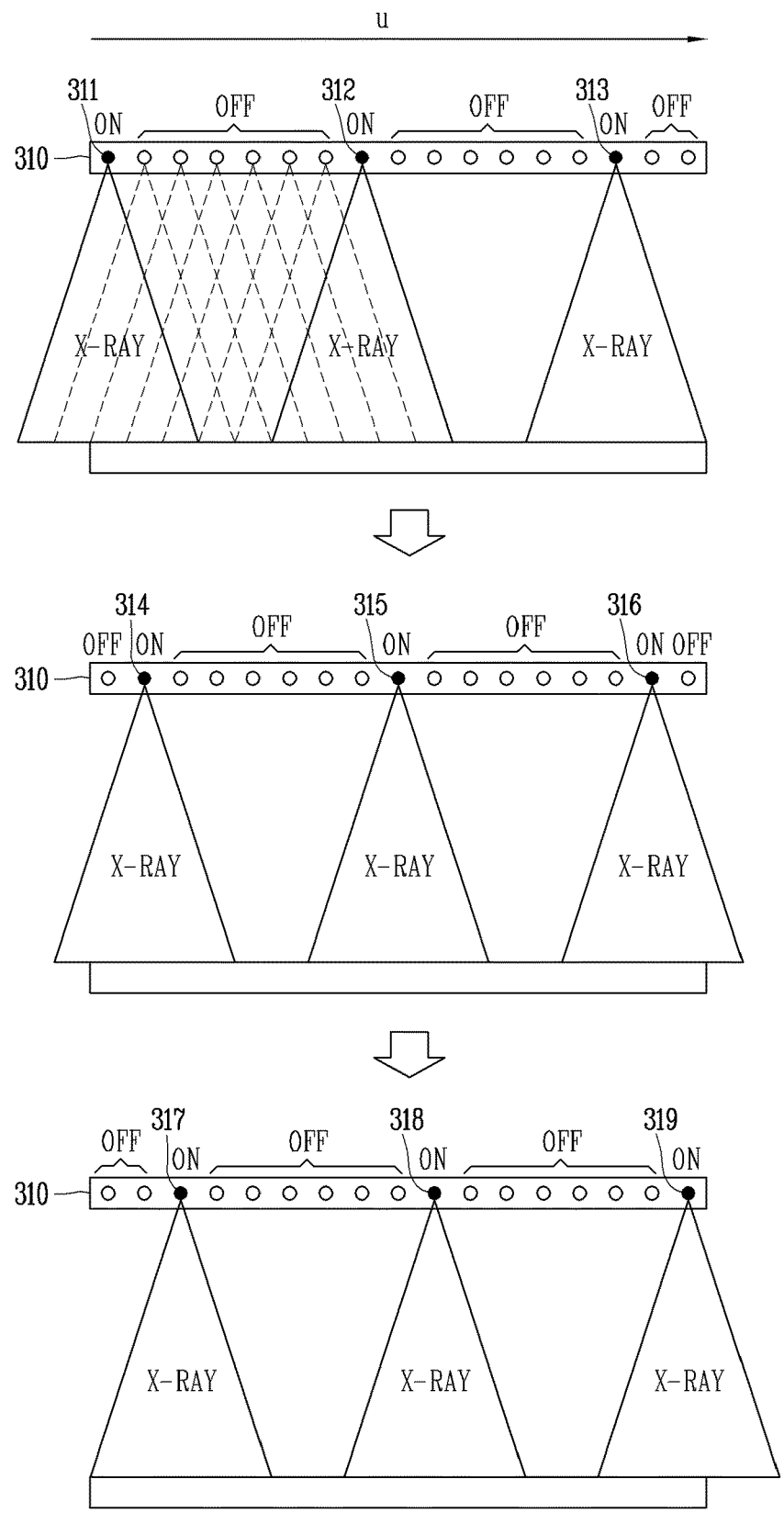
FIG. 3 is a diagram for explaining a method of capturing an X-ray image by performing on/off control on each of a plurality of X-ray sources according to an embodiment of the present disclosure.

FIG. 3 is a diagram for explaining a method of capturing a plurality of X-ray images by controlling turning on/off of a plurality of X-ray sources according to an embodiment of the present disclosure.

The X-ray imaging device 20 may capture an X-ray image of a subject to be imaged using a horizontal movement method along a first direction u by controlling turning on or off of each of the X-ray sources included in the X-ray generator 210.

The X-ray generator 210 operates at least one X-ray source for a certain time (e.g., several msec to hundreds of msec) while maintaining an interval of turning on of the X-ray sources so that X-rays radiated on the X-ray detector 230 are distributed not to overlap each other. The X-ray generator 210 may individually turn the X-ray sources on or off one by one when the X-rays are distributed to overlap each other.

The X-ray imaging device 20 may control only some X-ray sources to be turned on so that X-rays emitted from X-ray sources that are turned on do not redundantly capture the subject to be imaged. For example, the X-ray imaging device 20 may control a first X-ray source 311, a second X-ray source 312, and a third X-ray source 313 to be turned on, among the plurality of X-ray sources included in the X-ray generator 210, to capture the subject to be imaged.

Then, the X-ray imaging device 20 may control a fourth X-ray source 314, a fifth X-ray source 315, and a sixth X-ray source 316 to be turned on to capture the subject to be imaged. In addition, the X-ray imaging device 20 may control a seventh X-ray source 317, an eighth X-ray source 318, and a ninth X-ray source 319 to be turned to capture the subject to be imaged.

The X-ray imaging device 20 may transmit a certain signal to the X-ray detector 230 simultaneously when one or more X-ray sources are turned on, and obtain and store projection data whenever each of the X-ray sources are turned on.

Figure 4:
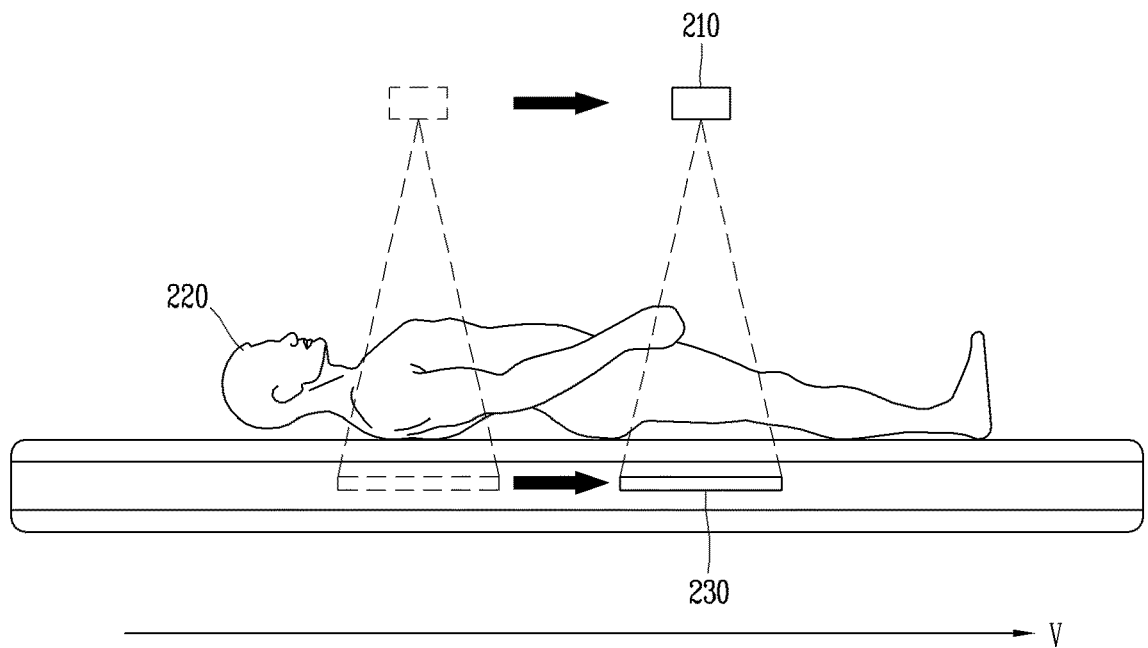
FIGS. 4 and 5 are diagrams for explaining a method of capturing an X-ray image using the X-ray imaging device according to an embodiment of the present disclosure.
Figure 5:
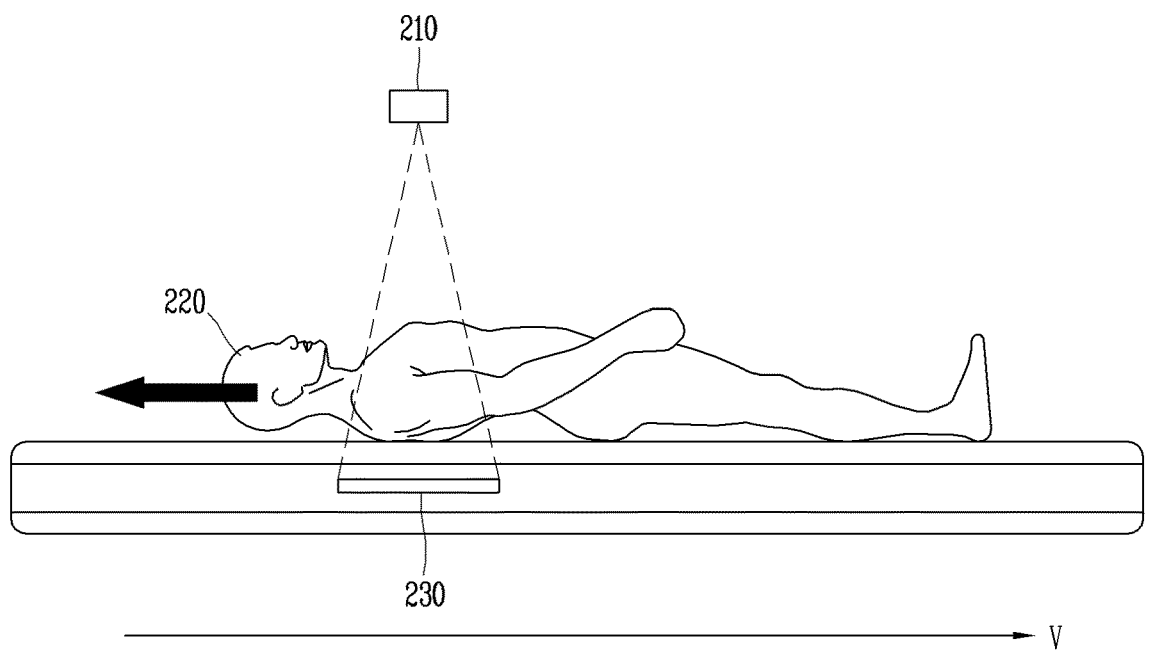

FIGS. 4 and 5 are diagrams for explaining a method of capturing an X-ray image using an X-ray imaging device according to an embodiment of the present disclosure.

Referring to FIG. 4, the X-ray imaging device 20 according to an embodiment of the present disclosure may capture an X-ray image of the subject 220 to be imaged, as the X-ray generator 210 or the X-ray detector 230 horizontally moves in a second direction v.

Alternatively, referring to FIG. 5, the X-ray imaging device 20 according to an embodiment of the present disclosure may capture an X-ray image of the subject 220 to be imaged, when the X-ray generator 210 or the X-ray detector 230 is fixed, as the subject 220 to be imaged horizontally moves in the second direction v.

Figure 6:
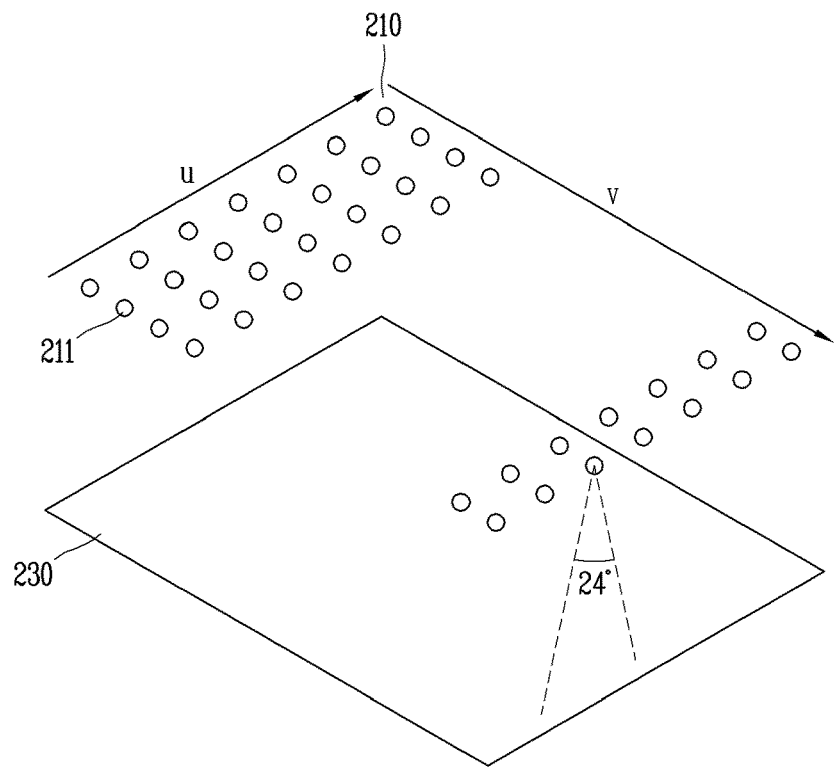
FIG. 6 is a diagram for explaining an X-ray generator in which the plurality of X-ray sources according to an embodiment of the present disclosure are arranged in a two-dimensional (2D) array form.

FIG. 6 is a diagram for explaining an X-ray generator in which a plurality of X-ray sources according to an embodiment of the present disclosure are arranged in a 2D array form.

A plurality of X-ray sources 211 in the X-ray generator 210 may be arranged in a 2D array form. The X-ray imaging device 20 may capture X-ray images by controlling each of the X-ray sources 211 in the first direction u or the second direction v. Accordingly, a subject to be imaged may be captured with a same effect as that of capturing an image when an X-ray generator in which a plurality of X-ray sources arranged in a one-dimensional (1D) line form moves horizontally.

Figure 7:
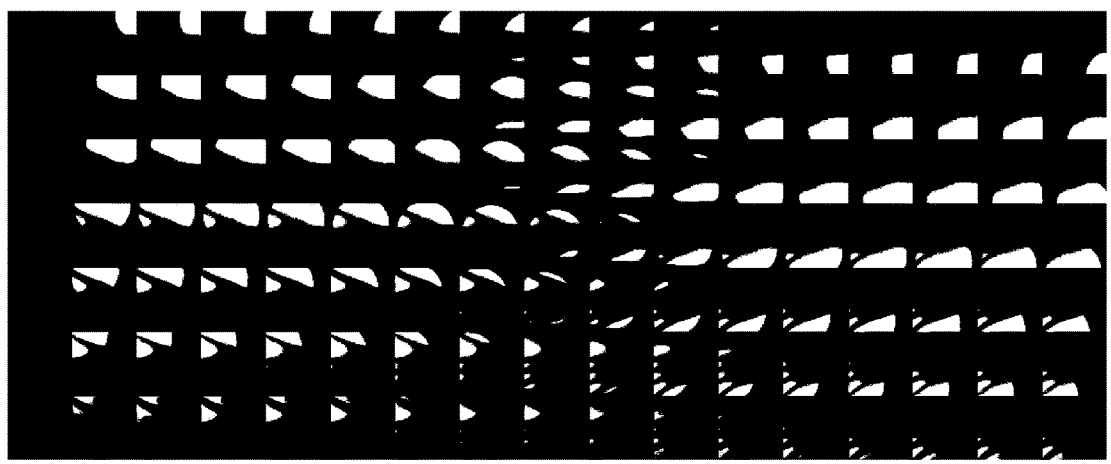
FIG. 7 is a diagram illustrating multiple pieces of projection data obtained by the X-ray imaging device according to an embodiment of the present disclosure.

FIG. 7 is a diagram illustrating multiple pieces of projection data obtained by an X-ray imaging device according to an embodiment of the present disclosure.

Multiple pieces of projection data 700 may be projection images on which X-rays detected by the X-ray detector 230 are projected after being emitted as a plurality of respective X-ray sources in the X-ray generator 210 are sequentially turned on or off in the first direction u or the X-ray generator 210 is horizontally moved in the second direction v.

The X-ray imaging device 20 may reconstruct a 2D or 3D X-ray image, i.e., a tomography image of a subject to be imaged on the basis of the multiple pieces of projection data 700.

Figure 8:
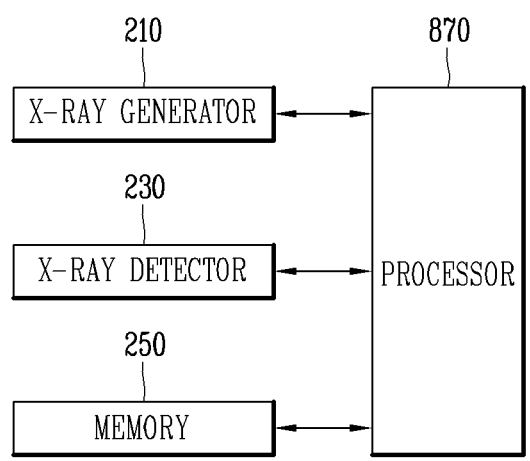
FIG. 8 is a block diagram for explaining the X-ray imaging device according to an embodiment of the present disclosure.

FIG. 8 is a block diagram for explaining an X-ray imaging device according to an embodiment of the present disclosure.

The X-ray imaging device 20 may include the X-ray generator 210, an X-ray detector 230, a memory 250, and a processor 870.

The X-ray generator 210 may include a plurality of X-ray sources. The X-ray sources may be arranged in a 1D line form or a 2D array form.

The X-ray detector 230 may generate an electrical signal corresponding to a transmitted X-ray dose. The X-ray detector 230 may generate projection data by generating an electrical signal.

The memory 250 may store a program for processing and controlling each signal in the processor 870, and store a signal-processed image, voice, a data signal, or the like. The memory 250 may store multiple pieces of projection data.

The processor 870 may control movement of the X-ray generator 210 or the X-ray detector 230 or turning on or off of each of the X-ray sources in the X-ray generator 210.

In addition, the processor 870 may store, in the memory 250, multiple pieces of projection data generated by the X-ray detector 230.

In addition, the processor 870 may reconstruct the multiple pieces of projection data as a tomography image of a subject to be imaged, i.e., a 2D or 3D X-ray image. For example, the processor 870 may generate a 2D or 3D X-ray tomography image by applying a certain reconstruction algorithm on the basis of the multiple pieces of projection data.

Filtered back projection (FBP) may be provided as a representative reconstruction algorithm. However, when the FBP reconstruction algorithm used in the tomosynthesis system 10 in the related art, as shown in FIG. 1, is used in the X-ray imaging device 20 of FIG. 2, a problem in which an artifact appears in a reconstructed X-ray image may occur. The tomosynthesis system 10 in the related art obtains projection data as an X-ray generator rotates with reference to a certain rotating shaft. On the other hand, the X-ray imaging device 20 of FIG. 2 horizontally moves to acquire projection data. Therefore, since X-rays are incident on a part of an X-ray detector at a limited angle, only a part of the projection data is used to calculate one pixel value, and thus, a discontinuous linear image artifact may appear in a reconstructed X-ray image.

FIGS. 9 to 13 are conceptual views for explaining a method of controlling the X-ray imaging device according to an embodiment of the present disclosure.

The X-ray generator 210 included in the X-ray imaging device in the present disclosure may include at least one X-ray source configured to radiate X-rays. As an example, a method of controlling the X-ray imaging device applied to the present disclosure may be identically/similarly derived and applied to an X-ray imaging device using various methods described with reference to FIGS. 1 to 6.

The X-ray detector 230 may generate multiple pieces of projection data by detecting X-rays emitted by the X-ray generator 210.

The processor 870 may generate a tomography image using the multiple pieces of projection data.

In this case, the processor 870 may control the X-ray generator to be in one mode among a first mode in which X-rays are radiated during a first radiation time and a second mode in which X-rays are radiated during a second radiation time corresponding to half of the first radiation time.

in the present disclosure, it is described that the second radiation time corresponds to half of the first radiation time, but the second radiation time is not limited thereto. The second radiation time only needs to be shorter than the first radiation time.

In addition, the processor 870 may generate a topography image on a basis of the multiple pieces of projection data generated through the X-ray detector 230.

Figure 9:
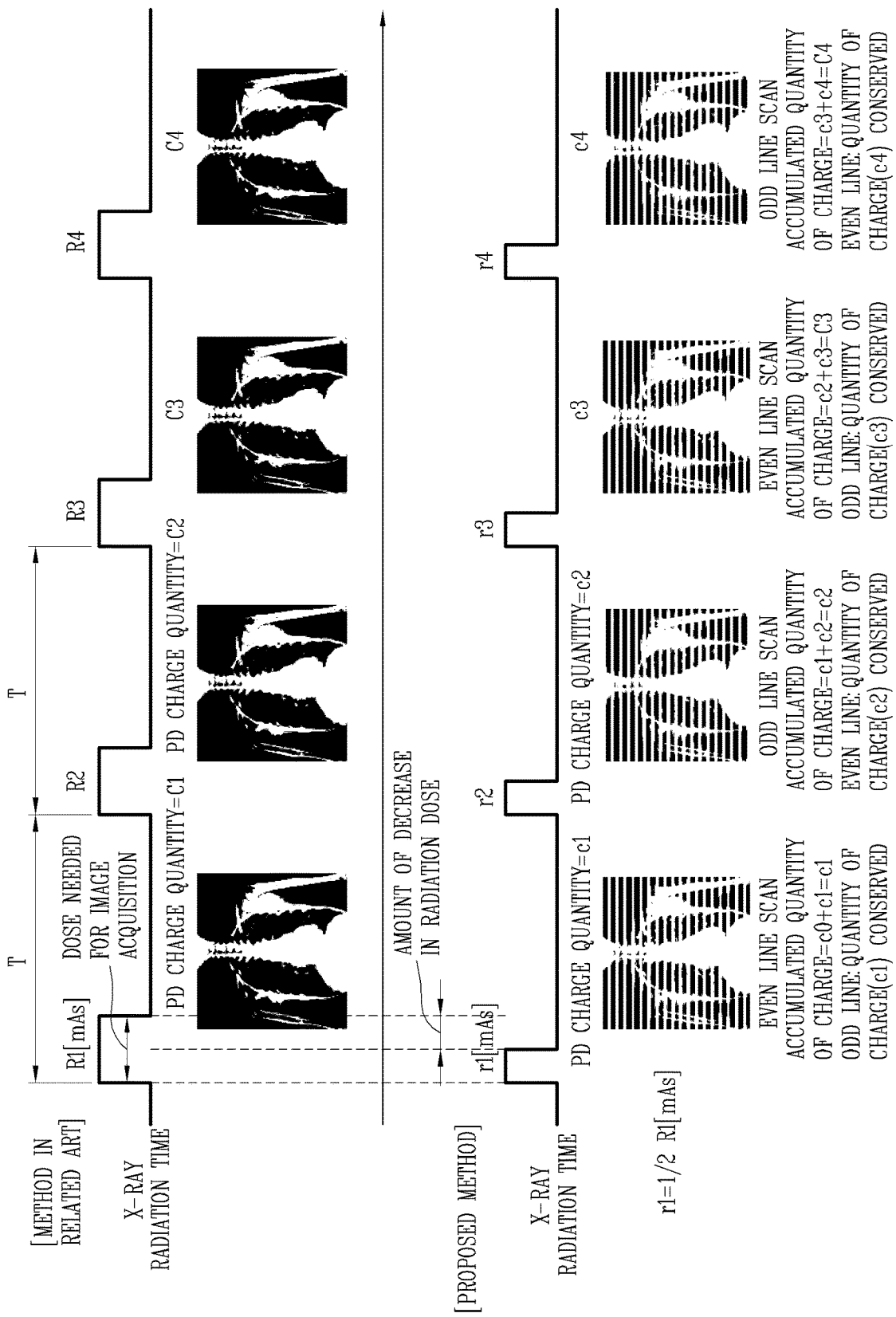
FIGS. 9 to 13 are conceptual views for explaining a method of controlling the X-ray imaging device according to an embodiment of the present disclosure.

Referring to FIG. 9, the processor 870 may radiate X-rays at a constant time interval T in the first mode and the second mode.

In this case, the processor 870 may control the X-ray generator 210 to radiate X-rays during a first radiation time R1 at a constant time interval T in the first mode.

The processor 870 may control the X-ray generator 210 to radiate X-rays during a second radiation time r1(r1=½*R1) corresponding to half of the first radiation time R1 at the constant time interval T in the second mode.

An X-ray source included in the X-ray generator may include a plurality of light-emitting devices configured to output X-rays.

Figure 12:
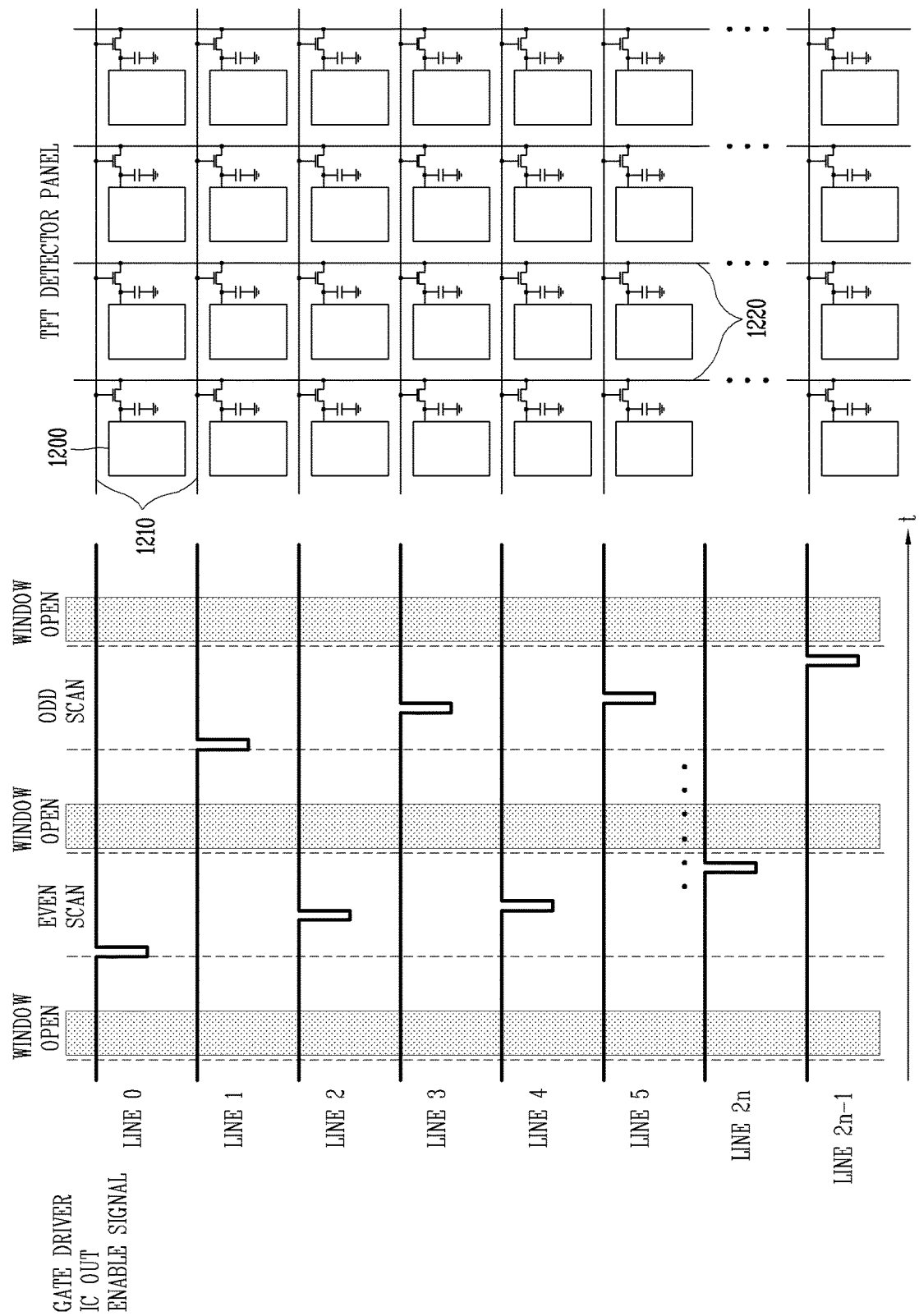

Referring to FIG. 12, the X-ray source may include a plurality of light-emitting devices. X-rays emitted from the light-emitting devices may be detected by thin-film transistor (TFT) detector panels that match the light-emitting devices, as shown in a right part of FIG. 12.

In addition, the X-ray source may include a plurality of gate lines LINE 0 to 2N configured to cause the light-emitting devices to emit light.

Referring to FIG. 12, in the second mode, the processor 870 may apply a signal to even gate lines EVEN SCAN among the gate lines LINE 0 to 2N during a first period, to radiate X-rays during the second radiation time r1 corresponding to half of the first radiation time R1.

In addition, the processor 870 may apply a signal to odd gate lines ODD SCAN among the gate lines LINE 0 to 2N during a second period that follows the first period.

In this case, when the processor 870 applies a signal to the even gate lines EVEN SCAN and the odd gate lines ODD SCAN, the signal may be applied sequentially to respective lines as illustrated in FIG. 12.

When the processor 870 applies a signal to the even gate lines EVEN SCAN and the odd gate lines ODD SCAN, the processor 870 may synchronize to activate X-ray detection panels 1200 corresponding to each line among a plurality of X-ray detection panels 1200 included in the X-ray detector 230.

For example, when the processor 870 applies a signal to the even gate lines EVEN SCAN among the gate lines LINE 0-2N, the processor 870 may apply a signal to a gate line 1210 to activate X-ray detection panels 1200 corresponding to the even gate lines EVEN SCAN, among the plurality of X-ray detection panels 1200. When the processor 870 applies a signal to the odd gate lines ODD SCAN, the processor 870 may apply a signal to the gate line 1210 to activate X-ray detection panels 1200 corresponding to the odd gate lines ODD SCAN.

Referring to FIG. 9, in the second mode, the processor 870 may acquire a first tomography image, on a basis of projection data obtained through an X-ray detector in a first period (EVEN LINE SCAN).

Then, a second tomography image may be obtained based on projection data acquired through the X-ray detector in a second period (ODD LINE SCAN).

Since gate lines activated by an X-ray source in the first tomography image are different from those activated by the X-ray source in the second tomography image, even when the X-ray source is in the same position, the first tomography image and the second tomography image may be captured as different images.

That is, the first tomography image may be a tomography image acquired by capturing only a part corresponding to even lines, and the second tomography image may be a tomography image acquired by capturing only a part corresponding to odd lines.

Accordingly, a part which is not captured in the first tomography image may be captured in the second tomography image, and a part which is not captured in the second tomography image may be captured in the first tomography image.

Then, the processor 870 may generate a final tomography image using the first and second tomography images.

In the first mode, a tomography image is captured at one time by activating all gate lines in each period.

Accordingly, as illustrated in FIG. 9, a dose c1 of X-rays emitted toward a subject in the second mode may correspond to half of a dose Cl of X-rays emitted toward the subject in the first mode (a method in the related art).

This is because gate lines activated in the second mode correspond to half of gate lines activated in the first mode in each period (odd or even).

In the present disclosure, through this configuration, since a dynamic X-ray detection device for X-ray video recording continuously radiates X-rays for a constant period to repeatedly acquire an image, a problem such as an increase in radiation exposure of a subject or patient to X-rays may be resolved.

The X-ray imaging device in the present disclosure may be the dynamic X-ray detection device for X-ray video recording, and ensure a dose of X-ray radiation needed to acquire an image while reducing a dose of X-ray radiation exposure, and thus, minimize deterioration in image quality.

In the present disclosure, the dynamic X-ray detection device for X-ray video recording may minimize deterioration in image quality while reducing a dose of X-ray radiation exposure to a half level.

To do so, in the present disclosure, when a detector panel included in the X-ray detector 230 performs a readout scan operation, odd lines may be distinguished from even lines to alternately read out odd line frames and even line frames in the units of a frame.

The processor 870 may maintain quantity of charge accumulated in odd- or even lines which have been skipped during the read out and, when the skipped odd- or even lines are read out, add the quantity of charge in the skipped odd- or even lines.

The processor 870 may generate (regenerate or recover) a final tomography image using a reconstruction algorithm employing neighboring odd line frames or even line frames, or both of odd and even frames.

Accordingly, in the present disclosure, the dynamic X-ray detection device for X-ray video recording may minimize a dose of X-ray radiation exposure and acquire high-quality X-ray images.

In addition, in the present disclosure, when a readout operation needed for image acquisition is performed, scan time may be shortened, and thus, the number of frames to be acquired per unit time may be increased and high-speed image acquisition may be ensured.

Referring to FIG. 12, the X-ray detector 230 in the present disclosure may include a dynamic X-ray detector that allows X-ray video recording and includes a detection panel having a light detection device array in a matrix structure, a gate driver integrated circuit (IC) 1210 configured to perform driving, and a readout IC 1220.

Here, in the present disclosure, lines of the detection panel may be divided into odd lines and even lines to independently read out only odd lines or even lines during a readout operation. In correspondence with this, the processor 870 may control a plurality of light-emitting devices included in an X-ray source to independently radiate X-rays with respect to the odd lines or the even lines.

According to the present disclosure, since only the odd lines or the even lines are read out, an image frame scan time may be reduced to ½, and thus, high-speed video recording may be performed.

Referring to FIG. 12, the X-ray generator performs radiation every time between an odd line readout operation and an even line readout operation, and a dose of X-ray radiation may be reduced to ½ of a general radiation dose or less.

The processor 870 may alternately perform an odd line image readout operation (at times of t, t+2, t+4, t+6, . . . ) and an even line readout operation (at times of t+1, t+3, t+5, t+7, . . . ).

The processor 870 may apply an out enable signal only to odd lines of the gate driver IC 1210 when odd lines are read out, and apply an out enable signal only to even lines of the gate driver IC 1210 when even lines are read out.

When the odd lines are read out after X-rays are radiated, the processor 870 conserves accumulated charge of a light-detection cell in the even lines. When the even lines in which the accumulated charge is conserved are read out, the processor 870 conserves accumulated charge of a light detection cell in the odd lines.

When the processor 870 reads out the odd lines, the processor 870 reads both of accumulated charge in the odd lines according to previously radiated X-rays (at the time t)

and conserved charge accumulated in the odd lines according to X-rays radiated before the previously radiated X-rays (at the time t−1).

In addition, when the processor 870 reads out the even lines, the processor 870 reads both of accumulated charge in the even lines according to previously radiated X-rays and conserved charge accumulated in the even lines according to X-rays radiated before the previously radiated X-rays.

The processor 870 may reconstruct a whole image using one or more neighboring odd line images or even line images, or the odd line images+the even line images, or the like, each acquired by the readout.

In addition, as illustrated in FIG. 12, the processor 870 may perform a flushing operation on odd lines or even lines between readout frames.

Figure 13:
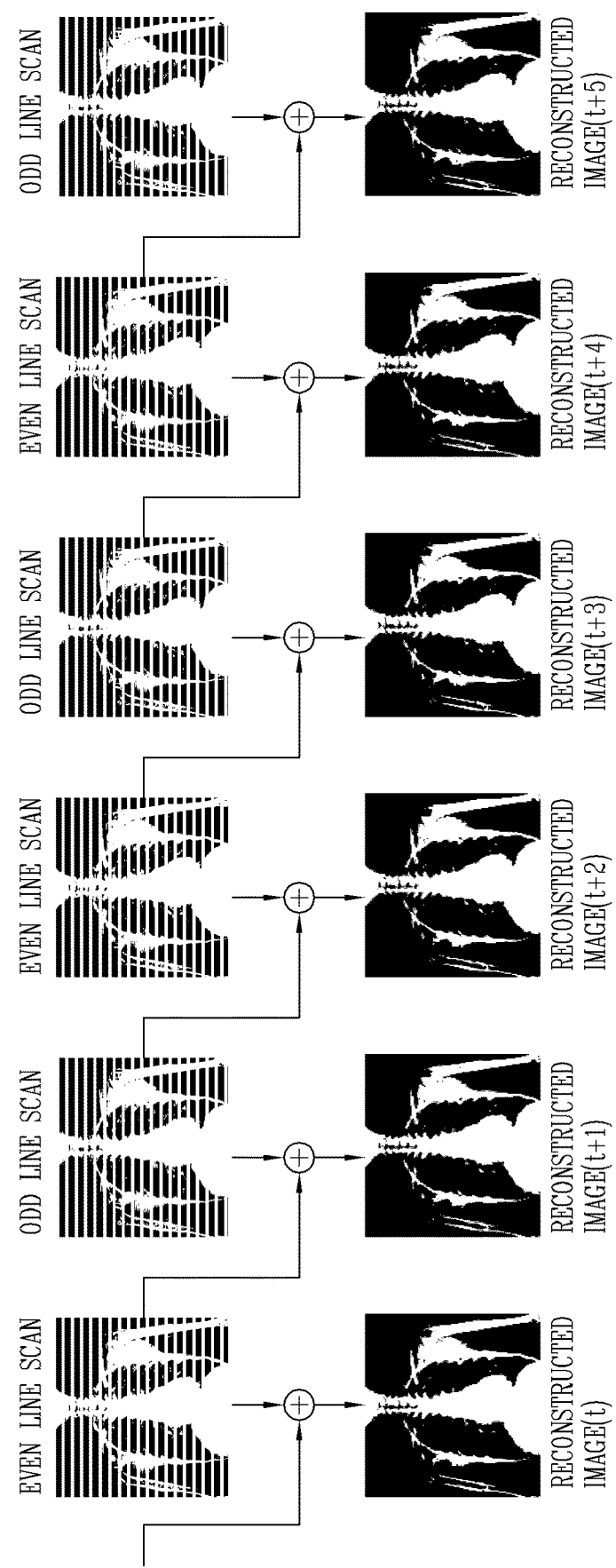

As illustrated in FIG. 13, the processor 870 in the present disclosure may generate a final tomography image using odd line images, even line images, or a combination thereof.

Meanwhile, the X-ray imaging device in the present disclosure may capture a tomography image using various controlling methods.

Figure 10:
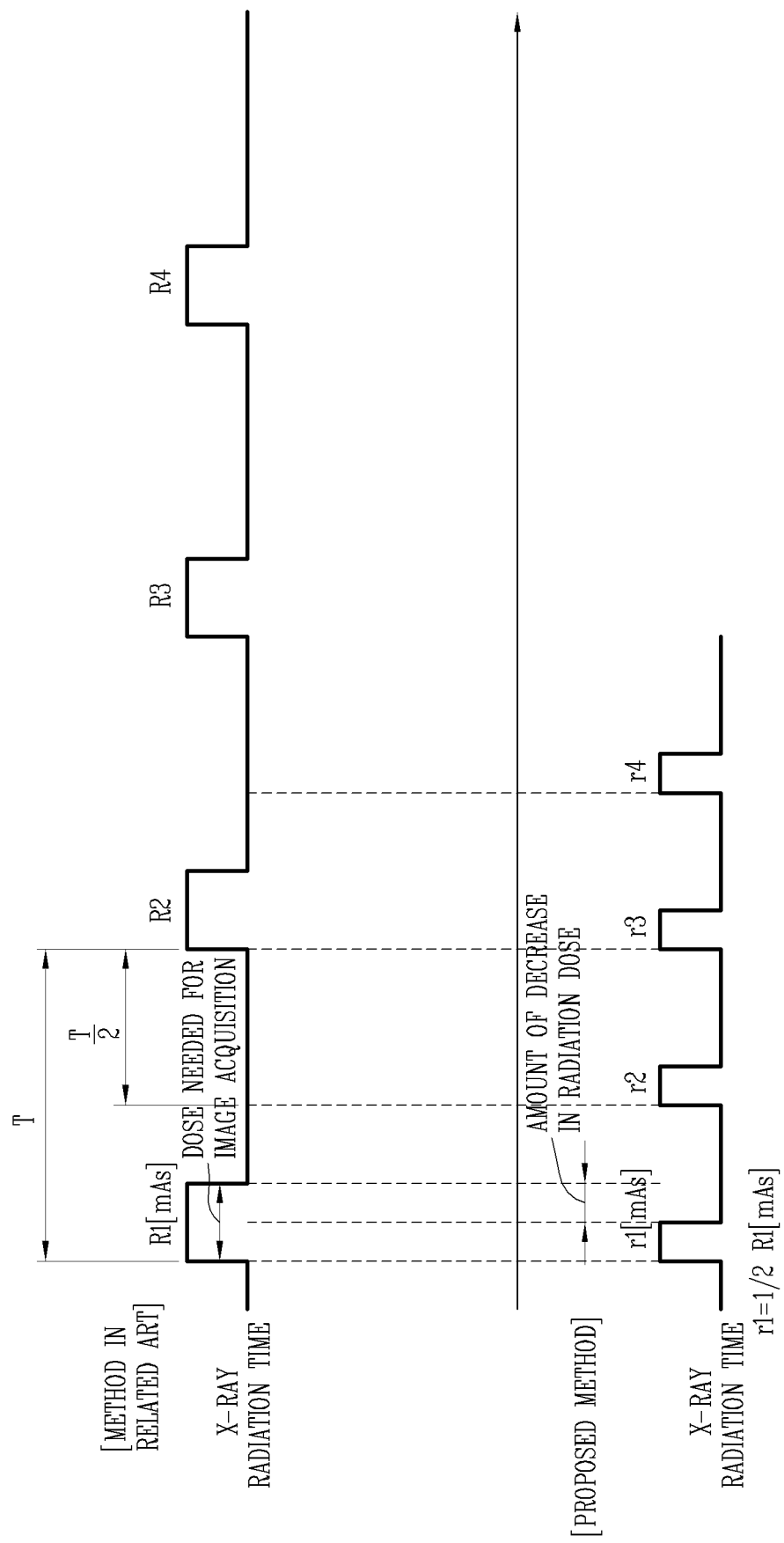

For example, as illustrated in FIG. 10, the processor 870 may control an X-ray generator in a third mode in which X-rays are radiated during the second radiation time r1 at a time interval corresponding to half T/2 of the constant time interval T.

In this case, as illustrated in FIG. 10, the first mode (in the method in the related art) and the third mode, X-rays may be radiated for a same number of times (e.g., four times in a case of FIG. 10).

Likewise, in the third mode, only even lines may be captured during the first radiation time, and only odd lines may be captured during the second radiation time to reduce a radiation time.

Alternate capturing of the even lines and the odd lines sequentially may be also performed in the second mode and the third mode.

Meanwhile, as illustrated in FIG. 10, in the third mode, the processor 870 may reduce a radiation time to a half, and also reduce an interval of X-ray radiation to a half (T/2).

This may be performed because even lines and odd lines are independently and sequentially controlled.

Then, the processor 870 may generate (regenerate or recover) a final tomography image using a first tomography image corresponding to the even lines and a second tomography image corresponding to the odd lines.

Accordingly, in the present disclosure, a time for capturing a tomography image may be reduced to nearly a half, and a dose of X-ray radiation to a subject may be reduced to a half.

Figure 11:
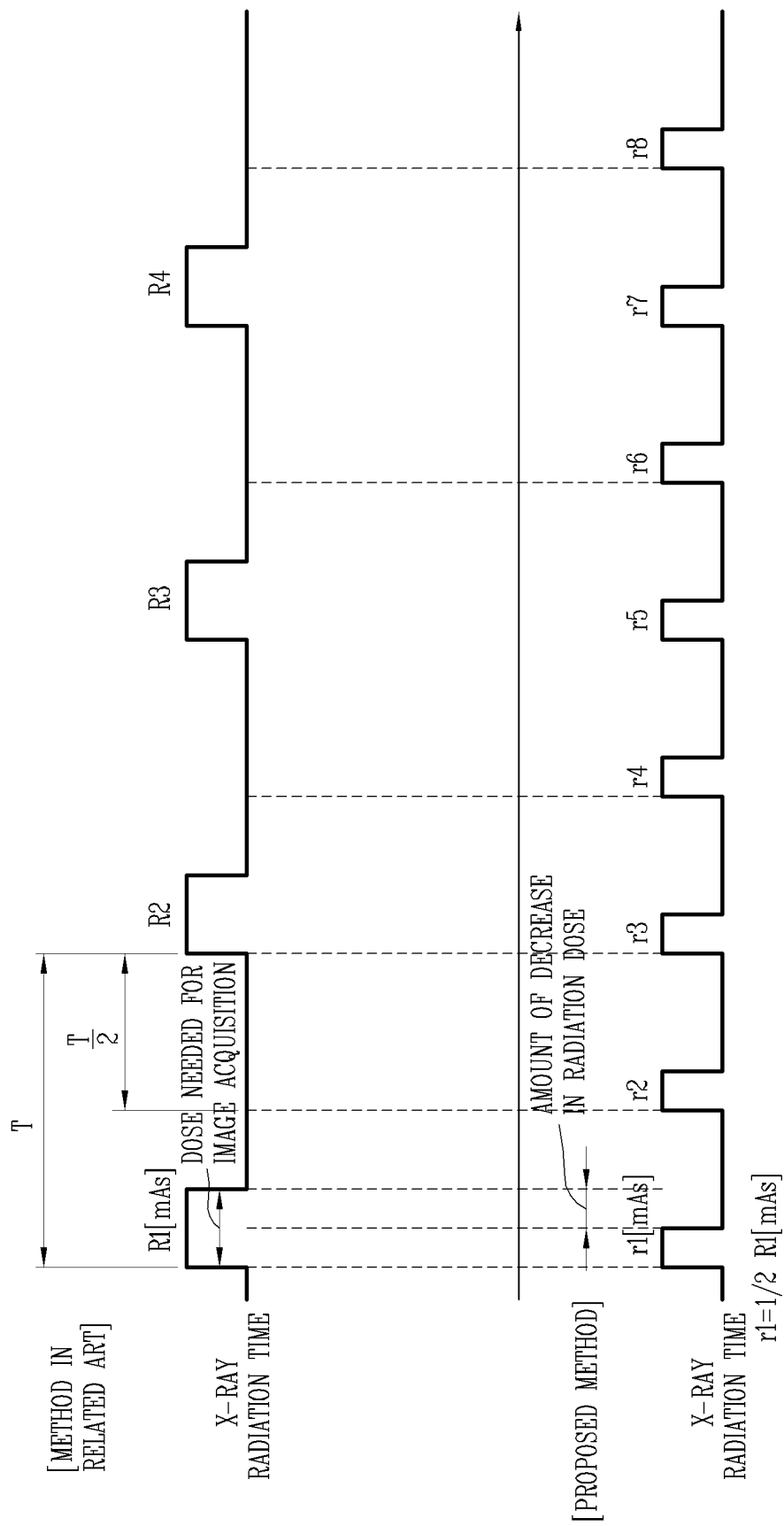

In another embodiment, as illustrated in FIG. 11, in the third mode (i.e., a mode in which a radiation time corresponds to half (r1) of that in the first mode and a radiation cycle corresponds to half (T/2) of that in the first mode), the processor 870 may control the X-ray generator 210 to radiate X-rays for a number of times in correspondence with twice a number of radiation times in the first mode.

In this case, the X-ray detector 230 may detect X-rays for the number of times twice that in the first mode, and the processor 870 may generate a tomography image using multiple pieces of detected projection data.

In this case, a total dose of X-ray radiation toward a subject may be similar to that in the method in the related art. However, since radiation times correspond to half in the method in the related art, a peak value of an X-ray radiated toward a subject in each radiation time may be reduced.

In addition, since large quantity of data is present in a captured tomography image, substantially same image quality as that in the method in the related art may be ensured.

The present disclosure can be implemented as computer-readable codes on a medium having a program recorded thereon. The computer-readable medium includes all kinds of recording devices in which data readable by a computer system is stored. Examples of the computer-readable medium include a hard disk drive (HDD), a solid state disk (SSD), a silicon disk drive (SDD), a ROM, a RAM, a CD-ROM, a magnetic tape, a floppy disk, an optical data storage device and the like, and may also be implemented in the form of a carrier wave (e.g., transmission over the Internet). The computer may include the control unit 180 of the terminal. The above detailed description should not be limitedly construed in all aspects and should be considered as illustrative. The scope of the present disclosure should be determined by reasonable interpretation of the appended claims, and all changes within the scope of equivalents of the present disclosure are included in the scope of the present disclosure.

The invention claimed is:

1. An X-ray imaging device comprising:
   an X-ray generator including at least one X-ray source configured to radiate X-rays;
   an X-ray detector configured to detect X-rays radiated from the X-ray generator; and
   a processor configured to:
      control the X-ray generator to radiate first X-rays for a first amount of radiation time according to a first mode,
      generate a first mode tomography image based on first mode projection data generated based on the first X-rays detected by the X-ray detector,
      control the X-ray generator to radiate second X-rays for a second amount of radiation time according to a second mode, and
      generate a second mode tomography image based on second mode projection data generated based on the second X-rays detected by the X-ray detector,
   wherein the second amount of radiation time is less than the first amount of radiation time.

2. The X-ray imaging device of claim 1, wherein the first X-rays are periodically radiated according to a first time interval in the first mode,
   wherein the second X-rays are periodically radiated according to a second time interval in the second mode, and
   wherein the second time interval is equal to approximately one half of the first time interval or the second amount of radiation time is equal to approximately one half of the first amount of radiation time.

3. The X-ray imaging device of claim 1, wherein the at least one X-ray source comprises:
   a plurality of light-emitting devices configured to output X-rays; and
   a plurality of gate lines configured to control the plurality of light-emitting devices to emit light,
   wherein the processor is further configured to:
   in the second mode, supply a signal to even gate lines among the plurality of gate lines during a first period to radiate a first set of X-rays, and supply a signal to odd gate lines among the plurality of gate lines during a second period subsequent to the first period to radiate a second set of X-rays.

4. The X-ray imaging device of claim 3, wherein the processor is further configured to:

in the second mode, acquire a first tomography image based on first projection data obtained through the X-ray detector during the first period, and acquire a second tomography image based on second projection data obtained through the X-ray detector during the second period, and generate a final tomography image based on the first tomography image and the second tomography image.

5. The X-ray imaging device of claim 3, wherein a dose of X-rays radiated toward a subject in the second mode corresponds to approximately half of a dose of X-rays radiated toward the subject in the first mode.

6. The X-ray imaging device of claim 2, wherein the first time interval in the first mode is approximately equal to the second time interval in the second mode, and
wherein the processor is further configured to:
in a third mode, periodically radiate third X-rays according to a third time interval, the third time interval being equal to approximately one half of the first time interval in the first mode and the second time interval in the second mode.

7. The X-ray imaging device of claim 6, wherein the processor is further configured to control the X-ray generator to radiate X-rays for a same number of times in the first mode and the third mode.

8. The X-ray imaging device of claim 6, wherein the processor is further configured to control the X-ray generator to radiate X-rays in the third mode twice as often as X-rays are radiated in the first mode.

9. A method of controlling an X-ray imaging device, the method comprising:
radiating, via an X-ray generator of the X-ray imaging device, first X-rays for a first amount of radiation time according to a first mode;
generating, via a processor of the X-ray imaging device, a first mode tomography image based on first mode projection data generated based on the first X-rays detected by the X-ray detector;
radiating, via the X-ray generator, second X-rays for a second amount of radiation time according to a second mode; and
generating, via the processor, a second mode tomography image based on second mode projection data generated based on the second X-rays detected by the X-ray detector,
wherein the second amount of radiation time is less than the first amount of radiation time.

10. The method of claim 9, wherein the first X-rays are periodically radiated according to a first time interval in the first mode,
wherein the second X-rays are periodically radiated according to a second time interval in the second mode, and
wherein the second time interval is equal to approximately one half of the first time interval or the second amount of radiation time is equal to approximately one half of the first amount of radiation time.

11. The method of claim 9, wherein the X-ray generator comprises:

a plurality of light-emitting devices configured to output X-rays; and
a plurality of gate lines configured to control the plurality of light-emitting devices to emit light,
wherein the method further comprises:
in the second mode, supplying a signal to even gate lines among the plurality of gate lines during a first period to radiate a first set of X-rays, and supplying a signal to odd gate lines among the plurality of gate lines during a second period subsequent to the first period to radiate a second set of X-rays.

12. The method of claim 11, further comprising:
in the second mode, acquiring a first tomography image based on first projection data obtained through the X-ray detector during the first period, and acquiring a second tomography image based on second projection data obtained through the X-ray detector during the second period; and
generating a final tomography image based on the first tomography image and the second tomography image.

13. The method of claim 11, wherein a dose of X-rays radiated toward a subject in the second mode corresponds to approximately half of a dose of X-rays radiated toward the subject in the first mode.

14. The method of claim 10, wherein the first time interval in the first mode is approximately equal to the second time interval in the second mode, and
wherein the method further comprises:
in a third mode, periodically radiating third X-rays according to a third time interval, the third time interval being equal to approximately one half of the first time interval in the first mode and the second time interval in the second mode.

15. The method of claim 10, wherein X-rays are radiated for a same number of times in the first mode and the second mode.

16. The method of claim 14, wherein X-rays in the third mode are radiated twice as often as X-rays radiated in the first mode.

17. The X-ray imaging device of claim 1, wherein the second amount of radiation time is approximately equal to one half of the first amount of radiation time.

18. The X-ray imaging device of claim 1, wherein the X-ray generator includes a plurality of X-ray sources arranged in a two-dimensional (2D) array or a one-dimensional (1D) array.

19. The X-ray imaging device of claim 18, wherein the processor is further configured to:
move the plurality of X-ray sources along a horizontal path.

20. The X-ray imaging device of claim 18, wherein the plurality of X-ray sources are fixed at a constant location, and
wherein the processor is further configured to:
in the second mode, periodically activate different subgroups of X-ray sources among the plurality of X-ray sources to emit simultaneous X-rays that do not overlap with each other.

* * * * *